(12) United States Patent
Snyder et al.

(10) Patent No.: US 9,994,870 B2
(45) Date of Patent: Jun. 12, 2018

(54) METHOD FOR GENERATING METHANE FROM A CARBONACEOUS FEEDSTOCK

(71) Applicant: UCHICAGO ARGONNE, LLC, Chicago, IL (US)

(72) Inventors: Seth W. Snyder, Lincolnwood, IL (US); Meltem Urgun-Demirtas, Naperville, IL (US); Yanwen Shen, Naperville, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 0 days. days.

(21) Appl. No.: 14/540,393

(22) Filed: Nov. 13, 2014

(65) Prior Publication Data

US 2016/0138048 A1    May 19, 2016

(51) Int. Cl.
    *C12P 5/02*      (2006.01)
    *B01D 53/04*     (2006.01)
    *C10L 3/08*      (2006.01)

(52) U.S. Cl.
    CPC .......... *C12P 5/023* (2013.01); *B01D 53/0423* (2013.01); *B01D 2253/102* (2013.01); *B01D 2256/245* (2013.01); *B01D 2257/304* (2013.01); *B01D 2258/05* (2013.01); *C10L 3/08* (2013.01); *Y02E 50/343* (2013.01); *Y02P 20/152* (2015.11); *Y02P 20/59* (2015.11)

(58) Field of Classification Search
    CPC ..................................................... C12P 5/023
    See application file for complete search history.

(56) References Cited

U.S. PATENT DOCUMENTS

| | | | |
|---|---|---|---|
| 6,117,672 A | 9/2000 | Breckenridge | |
| 7,883,884 B2 | 2/2011 | Bonde et al. | |
| 8,247,009 B2* | 8/2012 | Datta | B01D 53/84 426/56 |
| 8,361,200 B2 | 1/2013 | Sayari et al. | |
| 8,673,257 B2* | 3/2014 | Reddy | B01D 53/40 166/402 |
| 2009/0217575 A1 | 9/2009 | Raman et al. | |
| 2010/0107872 A1 | 5/2010 | Bethell | |
| 2013/0025188 A1* | 1/2013 | Cheiky | C10J 3/00 44/307 |
| 2013/0212935 A1 | 8/2013 | Heimann | |
| 2014/0183401 A1* | 7/2014 | Goletto | C04B 26/06 252/62 |

FOREIGN PATENT DOCUMENTS

| | | |
|---|---|---|
| CN | 101585522 B | 11/2009 |
| JP | 58196897 A | 11/1983 |
| WO | 2014057102 A1 | 4/2014 |

OTHER PUBLICATIONS

Craig, J.D., Completion of Final Report and Gas Analysis for a Biomass Gasifier, Cratech, Inc., 1-25 (2005).
Hrdlicka, J. et al., Parametric Gasification of Oak and Pine Feedstocks Using the TCPDU and Slipstream Water-Gas Shift Catalysis, NREL Technical Report (2008).
James, A.K. et al., Ash Management Review-Applications of Biomass Bottom Ash, Energies 5, 3856-3873 (2012).
Kloss, S. et al., Characterization of Slow Pyrolysis Biochars: Effects of Feedstocks and Pyrolysis Temperature on Biochar Properties, J. Environ. Qual. 41, 990-1000 (2011).
Mumme, J. et al., Use of Biochars in Anaerobic Digestion, Bioresource Technology 164, 189-197 (2014).
Peterson, J.R. et al., Aqueous Reaction of Fly Ash and Ca(OH)2 to Produce Calcium Silicate Absorbent for Flue Gas Desulfurization, Environ. Sci. Technol. vol. 22 (11), 1299-1304 (1988).
Torri, et al., Biochar Enables Anaerobic Digestion of Aqueous Phase from Intermediate Pyrolysis of Biomass, Bioresource Technology 172, 335-341 (2014).
Yuan, J-H. et al., The Forms of Alkalis in the Biochar Produced From Crop Residues at Different Temperatures, Bioresource Technology 102, 3488-3497 (2011).

* cited by examiner

Primary Examiner — Louise W Humphrey
Assistant Examiner — Stephen A Perkins
(74) Attorney, Agent, or Firm — Olson & Cepuritis, Ltd.

(57) ABSTRACT

The present invention provides a method for generating methane from a carbonaceous feedstock with simultaneous in situ sequestration of carbon dioxide to afford a biogas comprising at least 85 percent by volume methane, the method comprising anaerobically incubating a particulate additive in contact with a carbonaceous feedstock in a neutral or alkaline aqueous culture medium containing a culture of methanogenic consortia and collecting methane generated therefrom. The additive comprises at least one material selected from a biochar, an ash produced by gasification or combustion of a carbonaceous material, a black carbon soil, and a Terra Preta soil.

20 Claims, 4 Drawing Sheets

METHOD FOR GENERATING METHANE FROM A CARBONACEOUS FEEDSTOCK

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to methods for producing methane. More particularly, this invention relates to methods for biological generation of methane from a carbonaceous feedstock.

BACKGROUND OF THE INVENTION

Methane, the primary component of natural gas, is perhaps the most desirable fossil fuel. It is thermodynamically stable, has very high energy content, and is readily transportable with existing pipeline infrastructure. It is currently used in almost all energy applications, even as a transportation fuel. Methane is used to produce most of the world's ammonia as well as many other chemicals. In many parts of the world such as the U.S. natural gas production has not kept up with increased demand for this fungible energy source, which has a smaller carbon footprint than other fossil fuel sources. Methane is an important energy source used for power production, building heating, hot water, and cooking. Methane is also growing as a transportation fuel. In comparison to coal or petroleum, methane releases significantly smaller amounts of carbon dioxide per unit of energy produced.

Renewable sources for methane are increasingly important. Microbial conversion of carbonaceous feedstocks to methane by anaerobic bacteria and archaea is well known and used in many operations. Biogenic methane ("biogas") production is used in municipal wastewater treatment to convert sewage and activated sludge to methane to recover some of the energy and reduce the mass of waste sludge that has to be disposed. Methanogenesis is also used to treat waste from food, agricultural and chemical process industries to recover carbon and energy and reduce waste discharge loads and costs. In animal feedlots that are being increasingly used for poultry, swine and beef production, the wastes are digested to reduce discharge loads, recover some energy and reduce treatment costs. Numerous small scale digesters are used to treat human and other animal waste for the same reasons, especially in the rural areas of the less developed countries. In municipal solid waste landfills, biological methane production occurs after a period of time and now the more recent landfills are being designed and engineered to enhance biological methane production and recover energy values.

The main carbonaceous feedstocks that typically are utilized for biogas production include waste materials comprising one or more of (a) biopolymers, e.g., cellulose, hemicellulose, lignin, pectins, and the like; (b) fats and oils; (c) proteins; and (d) other soluble and semi-soluble organics. Based on numerous studies it is generally accepted that a consortia of anaerobic microorganisms e.g., hydrolytic acidogens, syntrophic acetogens, and methanogens, work together via highly self-regulated mechanisms to bring about this bioconversion.

Methanogenic microbial consortia naturally produce methane from a variety of carbonaceous sources. The energy content of the coal and other hydrocarbon materials is conserved in the produced methane. To balance the redox equation, $CO_2$ (as bicarbonate) is produced concomitantly, e.g., according to the formula: $2CH$ (e.g., coal)+ $2H_2O \rightarrow CH_4$ (for energy)+$CO_2$ (as $HCO_3^-$). This is a natural process that occurs in coal beds where coal bed methane (CBM) is produced, generally by the action of a consortium of anaerobic microbes typically in a biofilm around the coal surface. The same process occurs in any anaerobic fermentation of carbonaceous materials utilizing methanogenic microorganisms. A typical methane digester converting sewage or other carbonaceous feedstocks to methane produces a gas that is typically 50 to 70% methane, with the remaining 30 to 50% being predominantly $CO_2$, with trace amounts of other gases, including hydrogen sulfide. In July of 2014, the Untied States Environmental Protection agency (USEPA) ruled that biogas qualifies as a cellulosic biofuel.

There is an ongoing need for new methods of biogenic methane production, particularly methods that provide higher concentrations of methane and/or lower concentrations of undesirable gas contaminants such as carbon dioxide and hydrogen sulfide in the produced biogas. In addition, development of new sources for cellulosic biofuels and new energy sources are in the public interest. The methods described herein address these needs and interests.

SUMMARY OF THE INVENTION

The present invention provides a method for biological methane production from a carbonaceous feedstock to generate methane, while simultaneously sequestering carbon dioxide, and preferably hydrogen sulfide, in situ. The method comprises anaerobically incubating a particulate additive in contact with a particulate and/or dissolved carbonaceous feedstock in contact with a consortium of methanogenic microorganisms in an aqueous culture medium, and collecting biogas anaerobically generated therefrom. At least a portion of carbon dioxide produced during the incubation reacts with cations provided by the additive to prevent the carbon dioxide from evolving into the gas phase. The additive includes metal cations and is present in the culture medium at a concentration sufficient to sequester an amount of the carbon dioxide such that the methane content of the biogas is at least 85 percent by volume (vol %). The additive comprises one or more material selected from the group consisting of (i) a biochar produced from gasification or pyrolysis of a biomass material, (ii) an ash produced by gasification or combustion of a carbonaceous material, (iii) a black carbon soil, and (iv) a Terra Preta soil. The carbon dioxide generated during the incubation reacts with cations in the particulate additive to sequester the carbon dioxide. Preferably, the mixture is incubated at a temperature in the range of about 5 to about 70° C., more preferably about 10 to 65° C., and typically about 15 to about 55° C.

The additive preferably is provided in a concentration in the range of about 5 to 40 percent by weight (wt %) of volatile solid content of the carbonaceous feedstock. Preferably, the additive has a mean particle size in the range of about 0.01 to about 25 mm, more preferably 0.06 to about 9 mm as determined by sieve analysis.

The carbonaceous feedstock can be any suitable carbon-based material that can act as a nutrient source for methanogenic consortia. Preferably, the carbonaceous feedstock comprises biosolids from wastewater treatment, agricultural residues, manure, municipal waste, industrial waste, coal, tar sand, or any combination of two or more thereof. The methods described herein are particularly well suited for biological methane production from coal from the western United States, which contains relatively high levels of heavy metal contaminants, since the methane generated by the process is free from the heavy metal contaminants which remain in the aqueous culture, or are sequestered by the additive. Likewise, sulfur present in high-sulfur coal is sequestered or otherwise remains in the reactor during the biomethanation of high-sulfur coal in some embodiments of the processes described. Preferably, the carbonaceous feedstock (e.g., coal or waste materials) in the particulate mixture as a mean particle size in the range of about 0.01 to about 25 mm, more preferably 0.1 to about 1 mm.

The methods described herein are performed under anaerobic conditions with an aqueous culture of methanogenic bacteria and archaea or other methanogenic microorganisms under near neutral to mildly alkaline conditions (e.g., pH 6 to 10), preferably under mildly alkaline conditions. The alkaline conditions preferably are obtained by contact of the particulate additive with the aqueous culture medium. Preferably, the aqueous culture medium includes, or is in contact with, nutrients such as phosphates, nitrates, ammonium ion, other carbon sources, trace minerals, or any other nutrient that may be needed for the particular biological culture being utilized, in addition to the particulate additive and the carbonaceous feedstock. Non-limiting examples of suitable methanogenic microbial consortia include cultures obtained from coal fields and municipal waste facilities, municipal and industrial wastewater treatment facilities, landfills, manure pits, anaerobic digesters, anaerobic reactors, or isolated methanogenic cultures, which are capable of metabolizing high-carbon content to generate methane.

The methanogenesis process is performed under anaerobic conditions. Such conditions can be achieved by any method known in the art. One convenient method for achieving effective anaerobic conditions is to add an oxygen scavenging material (e.g., a reducing agent), such as sulfide ion (e.g. as $Na_2S$), to the culture medium to reduce any oxygen dissolved in the medium. Another method is to house a large volume of material in a closed reactor or vessel or an underground pit or cavern and let the biological culture consume the residual oxygen. Examples of these pits are coal mines or rock quarries.

During practice of the methods described herein, methanogenic microbial consortia convert carbonaceous materials into methane and carbon dioxide. At least some of the dissolved carbon dioxide produced during the process reacts with cations in the additive, such as alkaline earth cations, to form a carbonate salt, thus stripping the carbon dioxide from the methane gas. The additive also can react with other acidic gaseous materials that might be produced during the biomethanation, such as sulfur oxides, hydrogen sulfide, and the like, thus affording a high quality methane product, even from carbon feedstocks, such as high-sulfur coal.

Preferably, the particulate additive is present in the reactor in a quantity sufficient to maintain a basic pH in the culture medium and to sequester a substantial amount of the generated carbon dioxide, thus affording a biogas comprising at least about 85 vol %, methane, which has a carbon dioxide content of less than about 15 vol %, (more preferably less than about 10 vol %) based on the total volume of the produced gas, which provides environmental benefits, such as lowering the greenhouse gas content of the produced gas. The lower carbon dioxide content also decreases the need for subsequent purification of the biological methane required to achieve a pipeline quality natural gas. In addition, the present method has the benefit of transforming a high greenhouse gas-production capacity carbonaceous fuel such as coal, to produce a new fuel source having a lower intrinsic greenhouse gas production capacity when burned. In some embodiments the biogas is surprisingly substantially free from detectable hydrogen sulfide, particularly when the additive comprises a corn stover biochar material, which is high in potassium ion. Optionally, the additive can be supplemented with potassium ion, e.g., to achieve a potassium ion concentration in the range of about 50,000 to about 75,000 parts per million (ppm) in the additive, on a dry weight basis, or at least about 1,000 ppm in the culture medium in the biomethanation reactor.

The mixture can be incubated in a digester, reactor, vessel, septic system, pit, or cavern with enough fluid flow to mix the carbonaceous feedstock, particulate additive, and aqueous methanogenic microbial culture during the incubation. A suitable reactor should be able to achieve anaerobic conditions by either natural consumption of the residual oxygen or use of an oxygen scavenger. Such reactors can be one-stage, two-stage reactors or two-phase reactors. The reactor also preferably includes a gas collector to collect methane produced by the methanogenic consortia. Optionally, the reactor can include or be connected to a scrubber for removing residual amounts of carbon dioxide or other reactive contaminant gasses (e.g., sulfides) from the produced methane, although this generally is not necessary.

The following non-limiting embodiments further illustrate the methods described herein.

Embodiment 1 comprises a method for generating a biogas comprising at least 85 vol % methane from a carbonaceous feedstock, the method comprising the steps of: (a) anaerobically incubating a mixture of a carbonaceous feedstock in a neutral or alkaline aqueous culture medium containing a culture of methanogenic microorganisms and a particulate additive; and (b) collecting biogas generated therefrom; wherein at least a portion of carbon dioxide produced during the incubation reacts with cations provided by the additive to prevent the carbon dioxide from evolving into the gas phase; the additive is present in the culture medium at a concentration sufficient to sequester an amount of the carbon dioxide such the methane content of the biogas is at least 85 vol %, and the additive includes metal cations and comprises one or more material selected from the group consisting of (i) a biochar produced from gasification or pyrolysis of a biomass material, (ii) an ash produced by gasification or combustion of a carbonaceous material, (iii) a black carbon soil, and (iv) a Terra Preta soil.

Embodiment 2 comprises the method of embodiment 1, in which the additive comprises a potassium concentration of at least about 50,000 ppm on a weight basis (w/w).

Embodiment 3 comprises the method of any one of embodiments 1 and 2, in which the additive has been supplemented with a source of potassium ion to achieve a potassium concentration of at least about 1,000 ppm in the culture medium.

Embodiment 4 comprises the method of any one of embodiments 1 to 3, wherein the additive comprises sufficient alkaline earth metal ions to provide an alkaline earth metal ion concentration of at least about 1,500 ppm (w/w) in the culture medium.

Embodiment 5 comprises the method of any one of embodiments 1 to 4, wherein the additive also sequesters hydrogen sulfide and the collected biogas has a hydrogen sulfide content (i.e., concentration) of less than about 4 ppm on a volume basis (v/v).

Embodiment 6 comprises the method of any one of embodiments 1 to 5, wherein the collected biogas has a hydrogen sulfide content of less than about 5 parts per billion (ppb) (v/v).

Embodiment 7 comprises the method of any one of embodiments 1 to 6, wherein the concentration of additive is sufficient to provide collected biogas with a methane content of at least about 90 vol %.

Embodiment 8 comprises the method of any one of embodiments 1 to 7, wherein the concentration of additive is sufficient to provide collected biogas with a methane content of at least about 95 vol %.

Embodiment 9 comprises the method of any one of embodiments 1 to 8, wherein the additive comprises a biochar of a biomass material selected from the group consisting of gymnosperm plant material, angiosperm plant material, agricultural residue, municipal residue, industrial residue, algae, yeast and fungi.

Embodiment 10 comprises the method of any one of embodiments 1 to 9, wherein the additive comprises a corn stover biochar.

Embodiment 11 comprises the method of any one of embodiments 1 to 10, wherein the additive comprises an ash produced by gasification or combustion of at least one carbonaceous material selected from the group consisting of coal, a biomass material, a tar sand, a municipal solid waste, a leachate from a municipal waste, an industrial solid waste, a leachate from an industrial waste, biosolids from wastewater treatment, and manure.

Embodiment 12 comprises the method of any one of embodiments 1 to 11, wherein the carbonaceous feedstock comprises coal.

Embodiment 13 comprises the method of embodiment 12, wherein the coal is high-sulfur coal.

Embodiment 14 comprises the method of embodiment 13, wherein the coal contains heavy metals.

Embodiment 15 comprises the method of any one of embodiments 1 to 14, wherein the carbonaceous feedstock comprises tar sand.

Embodiment 16 comprises the method of any one of embodiments 1 to 15, wherein the carbonaceous feedstock comprises municipal waste, a leachate from a municipal waste, or a combination thereof.

Embodiment 17 comprises the method of any one of embodiments 1 to 16, wherein the carbonaceous feedstock comprises manure, biosolids from wastewater treatment, an agricultural residue, or a combination of two or more thereof.

Embodiment 18 comprises the method of any one of embodiments 1 to 17, wherein the mixture is incubated at a temperature in the range of about 10 to about 65° C.

Embodiment 19 comprises the method of any one of embodiments 1 to 18, wherein the culture of methanogenic consortia comprises one or more cultures from a coal bed methane produced water, a manure digester, a municipal waste, a sludge digester at wastewater treatment plant, an anaerobic reactor, or an isolated culture of methanogenic consortia.

Embodiment 20 comprises the method of any one of embodiments 1 to 19, wherein the mixture is incubated in a reactor comprising a system to restrict introduction of oxygen and for maintaining an aqueous environment, and is adapted to mix the particulate carbonaceous feedstock with the particulate additive, and the methanogenic microbial culture, and further includes a collector for collecting the biogas as it evolves.

Embodiment 21 comprises the method of any one of embodiments 1 to 20, wherein the aqueous culture medium has a pH in the range of about 6 to about 10.

Embodiment 22 comprises the method of any one of embodiments 1 to 21, wherein the additive material comprises porous particles that have a mean pore volume in the range of about 0.01 to about 1.25 $cm^3/g$, and an average pore diameter in the range of about 1 to 10 nm.

Embodiment 23 comprises the method of any one of embodiments 1 to 22, wherein the mixture is incubated in a coal seam, a coal mine, a large hole or quarry, a wastewater treatment plant, a solid waste digester, an anaerobic digester, an anaerobic reactor, septic system or a landfill.

Embodiment 24 comprises the method of any one of embodiments 1 to 23, wherein the additive has a mean particle size in the range of about 0.01 to about 25 mm.

Embodiment 25 comprises the method of any one of embodiments 1 to 24, wherein the carbonaceous feedstock is particulate and has a mean particle size in the range of about 0.01 to about 50 mm.

Embodiment 26 comprises the method of any one of embodiments 1 to 25, wherein the method further comprises collecting biosolids from the mixture after incubation, and applying the collected biosolids to soil as a fertilizer or soil amendment.

Embodiment 27 comprises the method of any one of embodiments 1 to 26, wherein the method further comprises collecting biosolids from the mixture after incubation, and applying the collected biosolids to soil as a fertilizer or soil amendment, and wherein the collected biosolids are enriched in Ca, Mg, Fe, P, K and or N relative to biosolids collected from a biomethanation under substantially the same conditions and with substantially the same feedstock, in the absence of the additive.

BRIEF DESCRIPTION OF THE DRAWINGS

The invention consists of certain novel features and a combination of parts hereinafter fully described, illustrated in the accompanying drawings, and particularly pointed out in various aspects of the invention, it being understood that various changes in the details may be made without departing from the spirit, or sacrificing any of the advantages of the described invention.

DETAILED DESCRIPTION OF PREFERRED EMBODIMENTS

Figure 1:
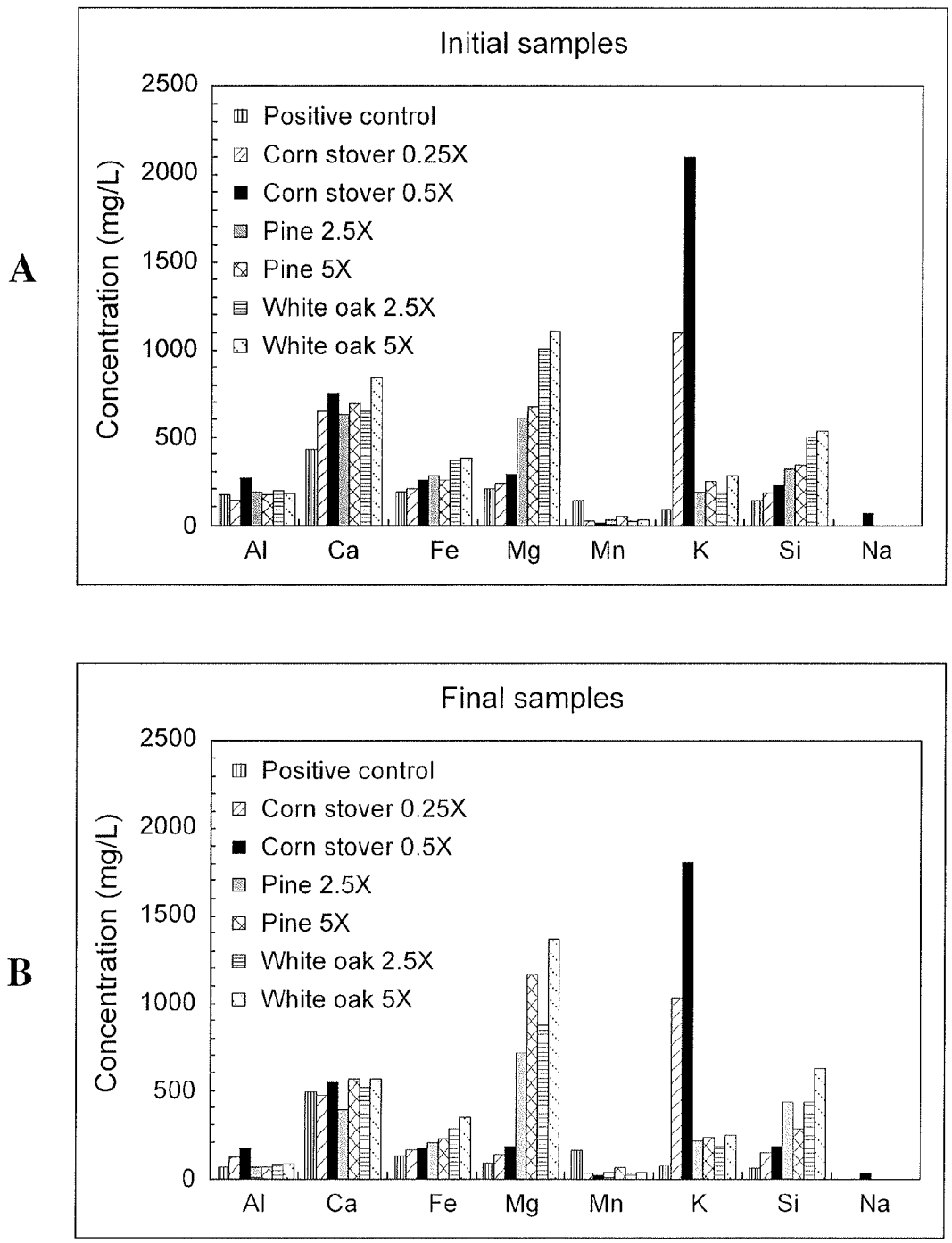
FIG. 1 bar graphs of initial (Panel A) and final (Panel B) metal ion metal concentrations for various biochar materials.

A method for generating methane-containing biogas from a carbonaceous feedstock with a reduced carbon dioxide concentration relative to conventional biogas methods is described herein. The method comprise anaerobically incubating one or more additive materials with a particulate and/or dissolved carbonaceous feedstock in reaction medium containing a culture of methanogenic consortia (e.g., at about 10 to about 65° C.), and collecting methane generated therefrom. Preferably the culture medium has a pH in the range of about 6 to 10. The additive material comprises the solid components of combustion or partial combustion of carbonaceous materials rich in cations. At least a portion of carbon dioxide produced during the incubation reacts with the cations to form bicarbonates and/or carbonates, thereby preventing carbon dioxide from evolving into the gas phase. The additive is present in a quantity sufficient to produce methane with a carbon dioxide content at least, e.g., about 50 vol % lower in comparison to a substantially similar method without the additive being present.

In some embodiments, the additive material is a biochar produced from gasification or pyrolysis of a biomass material. It is to be understood that some biochar may be converted to methane and carbon dioxide during the biomethanation reaction, as well. In other embodiments, the additive is an ash produced by combustion or partial combustion of a biomass material. Suitable biomass materials can be broadly classified into four categories, i.e., (i) gymnosperms (e.g., soft woods such as pine, spruce, fir, and cedar); (ii) angiosperms (e.g., monocots, including perennial grasses such as switchgrass, miscanthus, sorghum, sugarcane, and bamboo; herbaceous species such as corn, wheat, and rice); dicots, including flowering plants (e.g., alfalfa, soybean tobacco) and hardwoods (e.g., poplar, willow, and black locust); (iii) agricultural residue (e.g., such straws, hulls, stalks, shells and bagasse) and forest residue (e.g., dark and saw dust), municipal residue (biosolids, foodwaste); and (iv) algae, yeast and fungi used for porous activated carbon production.

As used herein, "biochar" refers to product obtained by thermal decomposition of a biomass material (e.g., carbohydrate, cellulosic, protein-containing, and/or fat-containing material, such as wood, agricultural residue, manure, and the like) under an atmosphere that is deficient in oxygen relative to normal air, or in the absence of oxygen/air. Biochars typically are porous materials that are carbon-rich, and generally also contain various levels of inorganic salts/minerals. The thermal decomposition generally is performed at a temperature of less than about 700° C. In contrast, the term "ash", as used herein, refers to the product of combustion or partial combustion of a biomass material (i.e., in the presence of air/oxygen), which results in a mineral-rich, carbon-poor material. Ashes also frequently are porous materials, and generally are basic.

The additive material preferably has high concentration of monovalent, divalent, and/or multivalent cations (e.g., a high concentration of potassium, calcium, magnesium, iron, and/or sodium). For example, the additive can have a high concentration of alkali metal ions (e.g., a K ion concentration in the range of about 0.25 mg/kg to about 100,000 mg/kg, or preferably about 53,000 mg/kg to about 71,000 mg/kg), alkaline earth metal ions (e.g., a Ca and/or Mg ion concentration in the range of about 25 to about 320,000 mg/kg, or preferably about 110,000 mg/kg to about 250,000 mg/kg), or transition metal ions (e.g., a Fe ion concentration in the range of about 5 mg/kg to about 30,000 mg/kg, or preferably about 1,200 mg/kg to about 12,000 mg/kg). In some embodiments, the additive material can be, e.g., black carbon or Terra Preta soils, which have high concentration of monovalent, divalent and/or multivalent cations. Suitable additive materials typically have a mean particle size in the range of about 0.01 to about 25 mm. Preferably, the additive material is a porous material and has a mean pore volume in the range of about 0.01 to about 1.25 cm$^3$/g and an average pore diameter in the range of about 1 to 10 nm.

In some embodiments, the carbonaceous feedstock comprises one or more of coal, biomass materials, municipal solid waste, a leachate from a municipal waste, agricultural residue, tar sand, sludge from municipal and/or industrial wastewater treatment operations, manure, urban waste, and carbonaceous waste leftover from an industrial process. In the case of particulate carbonaceous feedstocks, the materials preferably have a mean particle size in the range of about 0.01 to about 50 mm.

Preferably, the culture of methanogenic microorganisms comprises one or more cultures from coal bed methane produced-water, a manure digester, a solid waste digester, a sludge treatment digester or an anaerobic reactor in municipal or industrial wastewater treatment plant, or an isolated culture of a specific methanogenic microorganism.

The collected biogas is composed primarily of methane and has a carbon dioxide content of less than about 15 vol % based on the volume of the biogas.

Advantageously, both methane production and in situ sequestration of carbon dioxide and, optionally, hydrogen sulfide, can take place in the same reaction vessel, i.e., without the use of a separate scrubber. The incubation can be accomplished, e.g., in a reactor or digester under anaerobic conditions (i.e., conditions that restrict the intrusion of air or oxygen into the reactor) in a solution or slurry environment, and is adapted to include a mixture of the carbonaceous feedstock, the additive material, and the methanogenic consortium, and further includes a gas collection system to collect the biogas as it is formed during the anaerobic reaction. In some embodiments, the mixture can be incubated in a coal seam, a coal mine, a large hole or quarry, a wastewater treatment plant, a solid waste digester, an anaerobic digester, an anaerobic reactor, or a landfill.

The digestate (i.e., biosolids) produced during anaerobic biogas generation is a liquid slurry and/or solid product, which has increased "fertilizer value" (e.g., increased nitrogen, phosphorous, and potassium, also known as "NPK", as well as carbon, calcium, magnesium, and/or other nutrients) relative to the input materials (i.e., the carbonaceous feedstock and the additive), and can be used as a soil amendment or fertilizer.

Advantageously and surprisingly, additives comprising high levels of potassium (e.g., about 53,000 ppm to about 71,000 ppm of K ion), such as corn stover biochar, have been found to produce methane with very low levels (e.g., less than about 4 ppm by weight/volume or less than about 5 parts per billion (ppb) by volume) of hydrogen sulfide, which is a typical contaminant in anaerobic methane generation. Typically, hydrogen sulfide concentrations in the methane biogas are at least 90% lower in the methods described herein compared to anaerobic methane generation without the high potassium additive. Porous additive structures, such as are found in biochars are believed to promote the reaction between hydrogen sulfide and the additive components to sequester the hydrogen sulfide. $H_2S \rightarrow H+ HS^- \rightarrow S^-$ complexes with cations (e.g. FeS).

The present invention biologically converts coal or other carbonaceous feedstocks or wastes, under anaerobic conditions, to methane. In the present methods, $CO_2$ produced during biomethanation is captured and sequestered in situ by reaction with a particulate additive present in the culture medium (e.g., by reaction of carbon dioxide with cations present in the additive). For example, an additive comprising, potassium, calcium and/or magnesium salts (e.g., silicates, phosphates, and the like) is included within the reactor in very close proximity to coal particles or other carbonaceous feedstock materials that are being biomethanated. The process links the biological conversion (coal being converted to methane and carbon dioxide) to a novel sequestration mechanism (producing solid carbonate-enriched minerals), thus sequestering the $CO_2$:$HCO_3^-$+$Mg^{++}$→$MgCO_3$, or $HCO_3^-$+$Ca^{++}$→$CaCO_3$, or $HCO_3^-$+$K^+$→$KHCO_3$ or $K_2CO_3$. Rapid removal of $CO_2$ maintains a basic environment, very suitable for methanogenesis. Various other salts are produced as a byproduct when carbon dioxide reacts with the potassium, magnesium or calcium ions. In addition, rapid removal of carbon dioxide (while methane evolves to the gas phase) avoids product inhibition for the biological reactions.

The methods of the present invention utilize a combination of a particulate biochar, ash, or carbon-rich soil with a particulate and/or dissolved carbonaceous feedstock material, so that the relatively high surface area of the feedstock improves the efficiency of the biomethanation (biological methanogenesis) process and the relatively high surface area of the particulate additive improves the efficiency of $CO_2$ sequestration, in comparison to biomethanation in the absence of the additive.

Under anaerobic conditions, any sulfur in the coal remains reduced and SOx is not released to the atmosphere, a major environmental problem of many coals including Midwestern coal. In fact, sulfur is one of the primary limiting factors for Midwestern coal. Mercury and other heavy metals are a major environmental problem of Western coal, since these materials can be volatilized by combustion of the coal. In some embodiments, such as when potassium-rich additives (e.g., corn stover biochar) are used, there also is a surprising reduction in hydrogen sulfide in the produced biogas; frequently, hydrogen sulfide is undetectable. In the methods described herein heavy metal contaminants remain with the solids in the reactor or pit and are not released to the atmosphere. In addition, the particulate nature of the carbonaceous feedstock result in significantly increased biological methane generation rates.

The following examples illustrate certain aspects of the present invention, but are not meant to be limiting.

Materials and Methods

The anaerobic digestion experiments were conducted using 600-mL glass reaction vessels ("digesters") with a working volume of 550 mL. The reactors were flushed with helium to maintain anaerobic conditions. The volume of gas produced for the digester system was measured daily utilizing a gas collection system. A multi-layer foil gas sampling bag was attached to each reaction vessel to collect biogas samples (Restek, Bellefonte, Pa.). U.S. Pat. No. 8,247,009, which is incorporated herein by reference in its entirety, schematically illustrates a laboratory reactor system for biomethanation. The volume of biogas produced was measured using 100-mL high-performance gastight syringe (Hamilton, Reno, Nev.) or using an inline measurement system that measures the number of gas bubbles that passes a detector and correlates that to a gas volume. The experiments were conducted twice with three replicates at 37° C. (mesophilic conditions) and 55° C. (thermophilic conditions) to simulate conventional anaerobic digester operations at wastewater treatment plants. The headspace was sampled for methane content and the liquid samples (left over after digestion, namely digestate) were analyzed after the experiments were concluded. The methane ($CH_4$) and carbon dioxide ($CO_2$), and $H_2S$ content of biogas were determined by using gas chromatography (Shimadzu Scientific Instruments, Columbia, Md.) with a sulfur detector.

The inoculum and substrate sludge for anaerobic digestion were provided by from the Stickney Reclamation Plant of MWRD and Woodridge-Greene Valley wastewater treatment plant (WWTP) located in Woodridge, Ill. Stickney Plant operates mesophilic anaerobic digesters. The Woodridge-Greene Valley WWTP operates a two-stage temperature-phased anaerobic digestion system consisting of a mesophilic acid-stage digester and a thermophilic methane-stage digester. The inoculum was obtained from the thermophilic methane-stage digester. Biochar was generated, separated and collected from National Renewable Energy Laboratory's (NREL) pilot-scale pyrolysis reactor with corn stover, pine and white oak as the feedstocks. Operation of the NREL pyrolysis reactor is described in NREL Technical report NREL/TP-510-44577 ("Parametric Gasification of Oak and Pine Feedstocks Using the TCPDU and Slipstream Water-Gas Shift Catalysis"; Hrdlicka et al., December 2008), which is incorporated herein by reference in its entirety. The characteristics of biochar samples were determined using standard ultimate and proximate analysis and elemental analysis of ash.

Corn stover biochar included a concentration of about 9.2 mg/g of Ca and 8.3 mg/g of Mg. for comparison purposes, white oak biochar exhibited a Ca concentration of about 6.2 mg/g and a Mg concentration of about 110 mg/g; pine biochar exhibited a Ca concentration of about 4.2 mg/g and a Mg concentration of about 98 mg/g; and olivine has a Ca concentration of about 0.06 mg/g and a Mg concentration of about 307 mg/g.

Biochars are basic materials and afford pH values in the range of around 10 at a 5 g/100 mL concentration in water. FIG. 1 provides bar graphs of initial (Panel A) and final (Panel B) metal ion concentrations in mesophilic digesters provided by biochars from corn stover, pine and white oak at amounts of 0.5× for corn stover, and 2.5× and 5× for pine and white oak biochars, where × is the theoretical amount of Mg/Ca required to sequester 0.029 moles of carbon dioxide (the expected yield of produced carbon dioxide at the scale of the experiments, as described in more detail in EXAMPLE 1, below. The metal content in the digester environment is determined by using United States Environmental Protection Agency (USEPA) Method 200.7 (Revision 4.4), which is incorporated herein by reference in its entirety.

Tables 1 and 2 provide the compositional characteristics of the biochar materials. American Society for Testing and Materials (ASTM) ASTM D3172 and ASTM D 3176 methods, known as Proximate and Ultimate Analyses, were used to determine characteristics of biochar samples. Elemental analysis of ash samples was conducted using ASTM 3682.

TABLE 1

| Parameter | Composition | Corn stover | Pine | White oak |
|---|---|---|---|---|
| Ultimate | Moisture | 0.97 | 0.7 | 0.82 |
| | Ash | 45.18 | 18.69 | 34.9 |
| | S | 0.052 | 0.01 | 0.008 |
| | C | 52.78 | 60.04 | 59.49 |
| | H | 0.33 | 0.39 | 0.54 |
| | N | 0.5 | 0.26 | 0.18 |
| | O | 0.18 | 19.91 | 4.05 |
| Proximate | Moisture | 0.97 | 0.7 | 0.82 |
| | Ash | 45.18 | 18.69 | 34.9 |
| | Volatile Matter | 7.18 | 4.4 | 4.58 |
| | Fixed Carbon | 46.66 | 76.22 | 59.7 |

TABLE 2

| Parameter | Composition | Corn stover | Pine | White oak |
|---|---|---|---|---|
| Elemental Analysis of Ash | $SiO_2$ | 60.68 | 39.42 | 40.82 |
| | $Al_2O_3$ | 5.65 | 1.72 | 1.72 |
| | $TiO_2$ | 0.27 | 0.02 | 0.02 |
| | $Fe_2O_3$ | 1.93 | 6.76 | 6.80 |
| | $CaO$ | 3.87 | 1.78 | 2.29 |
| | $MgO$ | 4.23 | 44.93 | 43.33 |
| | $Na_2O$ | 0.74 | 0.09 | 0.05 |
| | $K_2O$ | 14.17 | 1.27 | 1.25 |
| | $P_2O_5$ | 2.19 | 0.53 | 0.13 |
| | $SO_3$ | 0.22 | 0.05 | 0.12 |
| | Cl | 1.01 | 0.01 | 0.01 |
| | $CO_2$ | 1.17 | 1.06 | 1.27 |

Example 1

Four corn stover biochar concentrations were tested to evaluate the effects of biochar on methane production from anaerobic digestion, along with a positive control with no additive, as shown in Table 3. Each digestion was conducted in triplicate. The selected amounts of biochar used in these experiments, shown in Table 3, represent about 0.25 to about 0.5 times the amount of biochar that theoretically would be required to sequester the entire amount of $CO_2$ produced during the anaerobic digestion (0.029 mole) if all sequestration resulted from reaction with divalent cations (Ca and Mg), e.g., as in U.S. Pat. No. 8,247,009. The amount of $CO_2$ produced for 550-mL anaerobic digestion (0.029 mole) was calculated based on preliminary results, while the concentration of divalent cations (Ca=8.3 mg/g, Mg=9.2 mg/g) in biochar were determined by using the ASTM Methods referred to above.

TABLE 3

Experimental conditions for batch-mode anaerobic digestion.

| Condition | Inoculum sludge (mL) | Substrate sludge (mL) | Biochar (g) |
|---|---|---|---|
| Positive control (without additive) | 111 | 45 | 0 |
| Corn stover biochar (0.25X) | 111 | 45 | 12.59 |
| Corn stover biochar (0.35X) | 111 | 45 | 17.63 |
| Corn stover biochar (0.42X) | 111 | 45 | 21.15 |
| Corn stover biochar (0.5X) | 111 | 45 | 25.18 |

Figure 2:
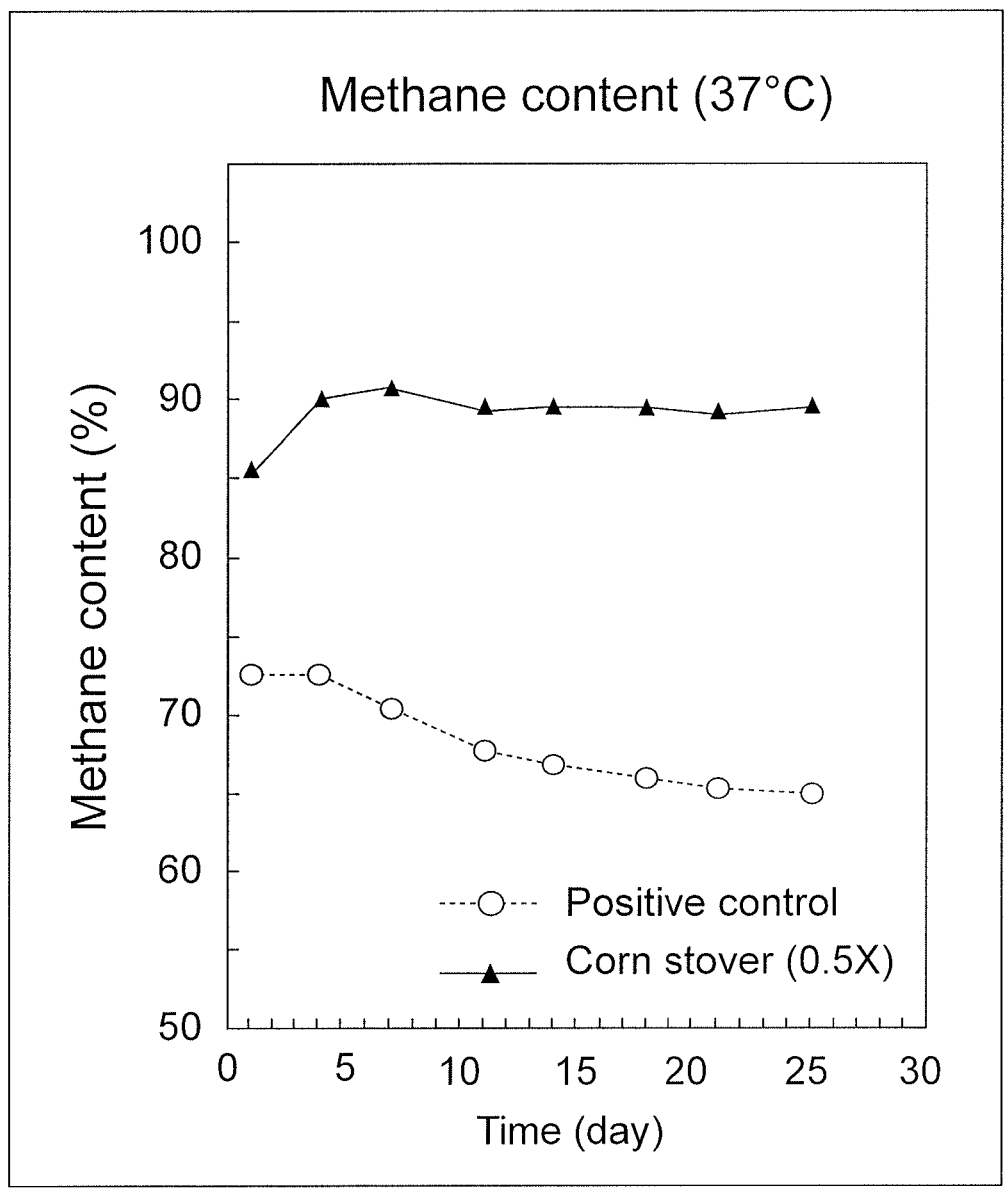
FIG. 2 provides plots of methane content (in vol %) versus time (in days) for biogas generated with and without a corn stover biochar additive under mesophilic anaerobic digestion conditions.
Figure 3:
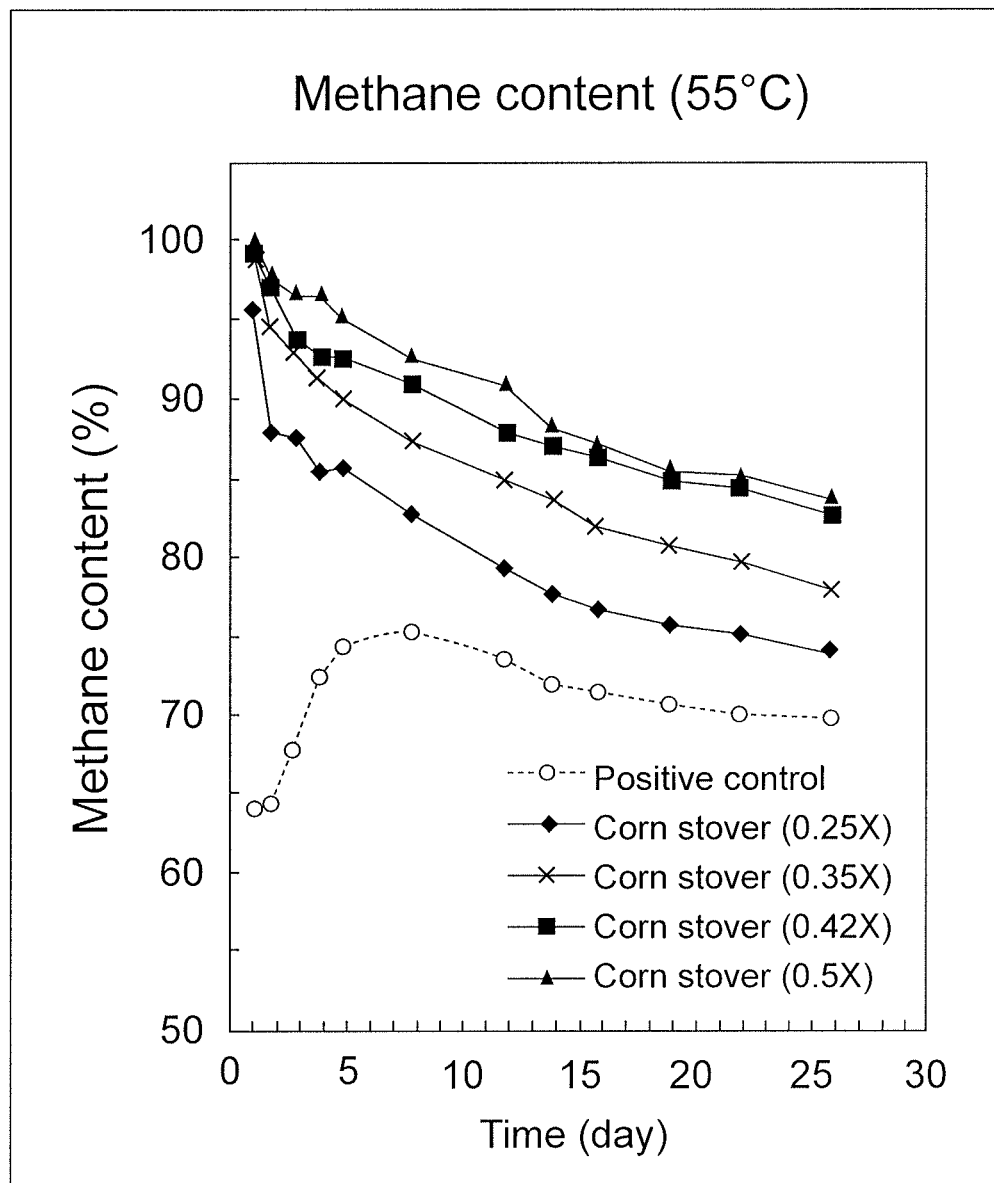
FIG. 3 provides plots of methane content (in vol %) versus time (in days) for biogas generated with and without a corn stover biochar additive at 4 different concentrations under thermophilic anaerobic digestion conditions.

X= theoretical amount of Mg/Ca required to sequester 0.029 moles of carbon dioxide Biogas generation data are shown in FIG. 2, FIG. 3 and Table 4. FIG. 2 provides plots of methane concentration in the generated biogas over time (in days) for biomethanation with corn stover at 0.5× compared to the positive control (no additive) under mesophilic conditions. The results in FIG. 2 indicate a dramatic and unexpected increase in methane content, which leveled off at about 90% after 5 days, compared to less than 70% methane for the control, indicating a significantly increased sequestration of carbon dioxide. FIG. 3 provides plots of methane concentration in the generated biogas over time (in days) for biomethanation with corn stover at various concentrations compared to the positive control (no additive) under thermophilic conditions. Table 4 provides numerical data for the runs under thermophilic conditions, up to 26 days. As in the case of mesophilic digestion, the results in FIG. 3 and Table 4 also show dramatic and unexpected increases in methane content relative to the control, reaching over 95% for the 0.5× level of corn stover biochar. These results are surprising and unexpected, since the level of divalent cations in the utilized amounts of corn stover biochar are significantly lower than the theoretical amount necessary to sequester the amount of carbon dioxide required to provide a methane content of greater than 90% if all of the sequestration were due to the Ca and Mg ions in the materials.

TABLE 4

| Day | Control | Corn stover (0.25X) | Corn stover (0.35X) | Corn stover (0.42X) | Corn stover (0.5X) |
|---|---|---|---|---|---|
| 1 | 64.0 | 95.7 | 99.0 | 99.3 | 100.0 |
| 2 | 64.3 | 88.0 | 94.7 | 97.0 | 98.0 |
| 3 | 67.7 | 87.7 | 93.0 | 93.7 | 96.7 |
| 4 | 72.3 | 85.3 | 91.3 | 92.7 | 96.7 |
| 5 | 74.3 | 85.7 | 90.0 | 92.7 | 95.3 |
| 8 | 75.3 | 82.7 | 87.3 | 91.0 | 92.7 |
| 12 | 73.7 | 79.3 | 85.0 | 88.0 | 91.0 |
| 14 | 72.0 | 77.7 | 83.7 | 87.0 | 88.3 |
| 16 | 71.3 | 76.7 | 82.0 | 86.3 | 87.0 |
| 19 | 70.7 | 75.7 | 80.7 | 85.0 | 85.3 |
| 22 | 70.0 | 75.0 | 79.7 | 84.3 | 85.0 |
| 26 | 69.7 | 74.0 | 78.0 | 82.7 | 83.7 |

These results also are important, because the methods described herein require a significantly lower loading of additive compared, e.g., to the method of U.S. Pat. No. 8,247,009, which thereby improves the economics of additive technology and lessens the space taken up by the additive in the digester, i.e., providing more efficient utilization of digester volume. Biochar additive, which also is used as a soil amendment, is beneficial to the fertilizer value of the biosolids. The presence of high potassium concentrations in porous corn stover biochar provided excellent process stability in the digesters, compared to other biochars, which are rich in divalent cations, but contain significantly less potassium ion. Other biochars can be supplemented with additional potassium to achieve similar results. While not wishing to be bound by theory, it is believed that this result may be due to the high buffering capacity, porosity and functionalized surface chemistry of the biochar. The addition of corn stover biochar rich in potassium accelerated the absorption of $CO_2$ and the resulting biogas was close to pipeline quality (>90% Methane and with non-detectable $H_2S$ concentration, i.e. <5 ppb (v/v)).

The addition of biochars into the digester environment also increased the fertilizer value of biosolids. FIG. 1 and Table 5 provide composition of digestate (biosolids) generated after digestion with biochars compared to the positive controls (no additives). The results in Table 5 indicate a dramatic increase in nutrient value of digestate, indicating a significant increase in fertilizer values.

TABLE 5

Nutrient Content of Digestate (mg/L)

| Condition | Ca | Fe | Mg | K | Total Nitrogen | Total Phosphorus |
|---|---|---|---|---|---|---|
| Positive control | 337 | 123 | 75 | 60 | 1333 | 881 |
| Corn stover 0.25X | 477 | 163 | 127 | 1033 | 1393 | 986 |
| Corn stover 0.5X | 547 | 177 | 173 | 1800 | 1553 | 1085 |
| Pine 2.5X | 383 | 203 | 710 | 180 | 1333 | 982 |
| Pine 5X | 563 | 213 | 1167 | 227 | 1607 | 1040 |
| White oak 2.5X | 517 | 270 | 860 | 170 | 1367 | 932 |
| White oak 5X | 573 | 333 | 1367 | 247 | 1633 | 1149 |
| Percentage improvement | Ca increase | Fe increase | Mg increase | K increase | N increase | P increase |
| Min | 14% | 32% | 68% | 183% | 0% | 6% |
| Max | 70% | 170% | 1714% | 2900% | 23% | 30% |

Reactors for Practicing the Invention.

Figure 4:
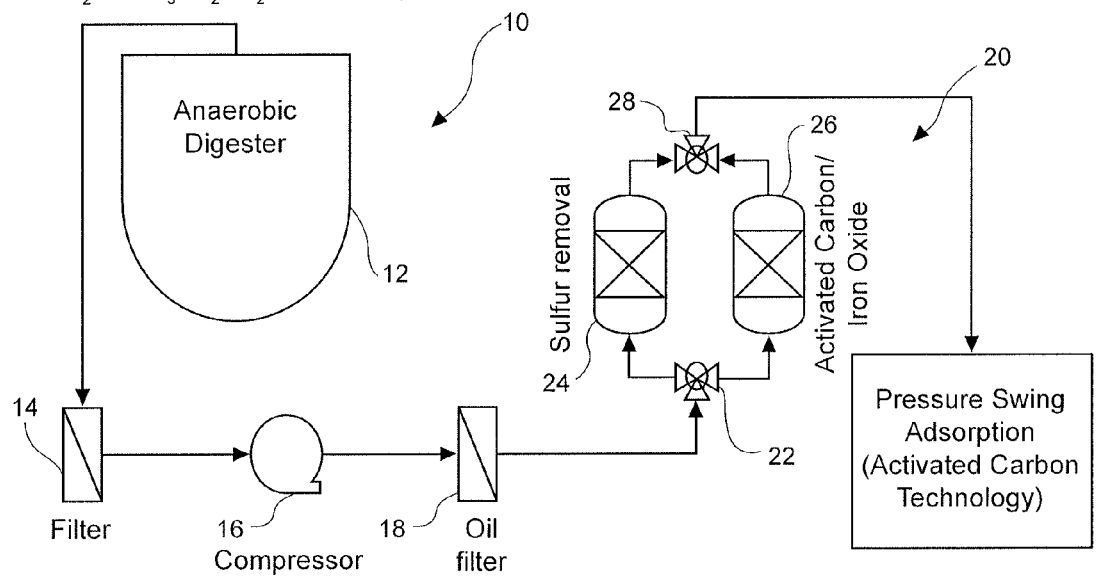
FIG. 4 provides a schematic diagram of a conventional reactor for biomethanation including a scrubber system.

FIG. 4 provides a schematic illustration of a conventional biomethanation reactor system 10, comprising a digester 12 operably connected to a gas filter 14. Filter 14 is connected to compressor 16, which feeds through oil filter 18 into scrubber system 20. Scrubber system 20 comprises a splitter valve 22 which feeds into sulfur removal scrubber 24 and scrubber 26 comprising activated carbon/iron oxide, the outputs of both of which feed into valve 28 to recombine the gas stream.

Figure 5:
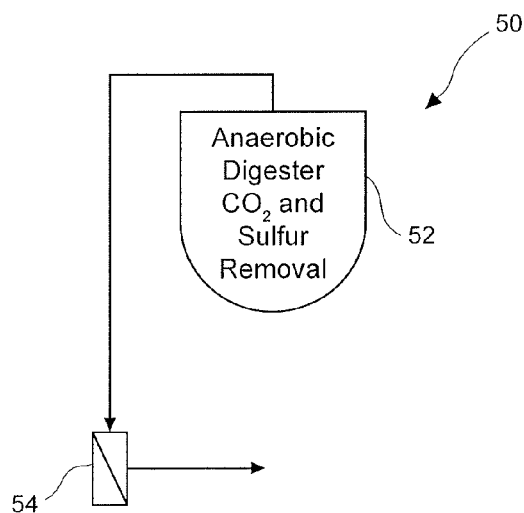
FIG. 5 provides a schematic diagram of a reactor for biomethanation according to the present invention, without a scrubber system.

FIG. 5 provides a schematic illustration of a conventional biomethanation reactor system 50, comprising a digester 52 operably connected to a gas filter 54, and without a scrubber system.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The embodiments of the invention in which an exclusive property or privilege is claimed are defined as follows:

1. A method for generating a biogas comprising at least 85 percent by volume (vol %) methane from a carbonaceous feedstock, the method comprising the steps of:
   (a) providing a carbonaceous feedstock having a volatile solids content;
   (b) preparing a mixture of the carbonaceous feedstock and a particulate additive in a neutral or alkaline aqueous culture medium containing a culture of methanogenic microorganisms;
   (c) anaerobically incubating the mixture from step (b); and
   (d) collecting biogas comprising methane generated in step (c);
   wherein:
   (1) the additive is present in the culture medium at a concentration of about 5 percent by weight (wt %) to about 40 wt % of the volatile solid content of the carbonaceous feedstock of step (a);
   (2) the additive includes alkali metal and alkaline earth metal cations; and comprises one or more materials selected from the group consisting of:
      (i) a biochar produced from gasification or pyrolysis of a biomass material,
      (ii) an ash produced by gasification or combustion of a carbonaceous material,
      (iii) a black carbon soil, and
      (iv) a Terra Preta soil;
   (3) at least a portion of carbon dioxide produced during step (c) reacts with the cations in the additive to prevent the carbon dioxide from evolving into the gas phase; and
   (4) the collected biogas from step (d) comprises at least 85 vol % methane and less than about 4 parts per million (ppm) (v/v) hydrogen sulfide.

2. The method of claim 1, wherein the additive comprises a potassium concentration of at least about 53,000 parts per million (ppm) (w/w).

3. The method of claim 2, wherein the additive has been supplemented with a source of potassium ion to achieve a potassium concentration of at least about 1,000 ppm (w/w) in the culture medium.

4. The method of claim 1, wherein the additive comprises sufficient alkaline earth metal ions to provide an alkaline earth metal ion concentration of at least about 1,500 ppm (w/w) in the culture medium.

5. The method of claim 1, wherein the collected biogas comprises less than about 5 parts per billion (ppb)(v/v) hydrogen sulfide.

6. The method of claim 1, wherein the collected biogas comprises at least about 90 vol % carbon dioxide.

7. The method of claim 1, wherein the collected biogas comprises at least about 95 vol % carbon dioxide.

8. The method of claim 1, wherein the additive comprises a biochar of at least one biomass material selected from the group consisting of gymnosperm plant material, angiosperm plant material, agricultural residue, algae, yeast and fungi.

9. The method of claim 1, wherein the carbonaceous feedstock comprises municipal waste, a leachate from a municipal waste, or a combination thereof.

10. The method of claim 1, wherein step (c) is performed at a temperature in the range of about 10° C. to about 65° C.

11. The method of claim 1, wherein the culture of methanogenic microorganisms comprises one or more cultures from a coal bed methane produced water, a manure digester, a municipal waste, an activated sludge from wastewater treatment, or an isolated culture of an individual methanogenic microbial consortia.

12. The method of claim 1, wherein step (c) is performed in an anaerobic digester comprising a system to restrict introduction of oxygen and for maintaining an aqueous environment, and is adapted to mix a particulate carbonaceous feedstock with the particulate additive, and the methanogenic microorganisms, and further includes a collector for collecting the biogas as it evolves.

13. The method of claim 1, wherein the aqueous culture medium has a pH in the range of about 6 to about 10.

14. The method of claim 1, wherein the additive comprises porous particles that have a mean pore volume in the range of about 0.01 cm$^3$/g to about 1.25 cm$^3$/g, and an average pore diameter in the range of about 1 nm to 10 nm.

15. The method of claim 1, wherein step (c) is performed in a coal seam, a coal mine, a large hole or quarry, a wastewater treatment plant, a solid waste digester, an anaerobic digester, an anaerobic reactor or a landfill.

16. The method of claim 1, wherein the particulate additive has a mean particle size in the range of about 0.01 mm to about 25 mm.

17. The method of claim 1, wherein the carbonaceous feedstock is particulate and has a mean particle size in the range of about 0.01 mm to about 50 mm.

18. The method of claim 1, further comprising collecting biosolids from the mixture after incubation, and applying the collected biosolids to soil as a fertilizer or soil amendment.

19. The method of claim 1, wherein the method further comprises collecting biosolids from the mixture after incubation, and applying the collected biosolids to soil as a fertilizer or soil amendment, and wherein the collected biosolids are enriched in Ca, Mg, Fe, P, K and or N relative to biosolids collected from a biomethanation under the same conditions and with the same feedstock, in the absence of the additive.

20. A method for generating a biogas comprising at least 85 percent by volume (vol %) methane from a carbonaceous feedstock, the method comprising the steps of:
    (a) providing a particulate carbonaceous feedstock having a volatile solids content;
    (b) preparing a mixture of the carbonaceous feedstock and a particulate biochar additive in a neutral or alkaline aqueous culture medium containing a culture of methanogenic microorganisms;
    (c) anaerobically incubating the mixture in an anaerobic digester comprising a system to restrict introduction of oxygen and for maintaining an aqueous environment, and which is adapted to mix the particulate carbonaceous feedstock with the particulate additive and the methanogenic microorganisms; and
    (d) collecting biogas comprising methane generated in step (c);
    wherein:
        (1) the additive is present in the mixture at a concentration of about 5 percent by weight (wt %) to about 40 wt % of the volatile solid content of the carbonaceous feedstock of step (a);
        (2) the additive includes alkali metal and alkaline earth metal cations;
        (3) at least a portion of carbon dioxide produced during step (c) reacts with the cations in the additive to prevent the carbon dioxide from evolving into the gas phase; and
        (4) the collected biogas of step (d) comprises at least 85 vol % methane, and less than about 4 parts per million (ppm) (v/v) hydrogen sulfide.

* * * * *

UNITED STATES PATENT AND TRADEMARK OFFICE
CERTIFICATE OF CORRECTION

PATENT NO. : 9,994,870 B2
APPLICATION NO. : 14/540393
DATED : June 12, 2018
INVENTOR(S) : Seth W. Snyder, Meltem Urgun-Demirtas and Yanwen Shen Page 1 of 1

It is certified that error appears in the above-identified patent and that said Letters Patent is hereby corrected as shown below:

On the Title Page

After Abstract: replace 20 Claims, 4 Drawing Sheets with 27 Claims, 4 Drawing Sheets In the Claims Please add the following claims:
-- 21. The method of claim 1, wherein the additive comprises a corn stover biochar.

22. The method of claim 1, wherein the additive comprises the ash and the carbonaceous material from which the ash is produced is selected from the group consisting of coal, a biomass material, a tar sand, a municipal solid waste, a leachate from a municipal waste, biosolids from wastewater treatment, and manure.

23. The method of claim 1, wherein the carbonaceous feedstock comprises coal.

24. The method of claim 23, wherein the coal is high-sulfur coal.

25. The method of claim 24, wherein the coal contains heavy metals.

26. The method of claim 1, wherein the carbonaceous feedstock comprises tar sand.

27. The method of claim 1, wherein the carbonaceous feedstock comprises manure, biosolids from wastewater treatment, an agricultural residue, algae, algal residues, or a combination of two or more thereof. --

Signed and Sealed this
Eighteenth Day of September, 2018

Andrei Iancu
*Director of the United States Patent and Trademark Office*